(12) United States Patent
Anferov et al.

(10) Patent No.: US 10,485,995 B2
(45) Date of Patent: Nov. 26, 2019

(54) COMPACT LIGHTWEIGHT HIGH-PERFORMANCE PROTON THERAPY BEAMLINE

(71) Applicants: Varian Medical Systems, Inc., Palo Alto, CA (US); Varian Medical Systems Particle Therapy GmbH, Troisdorf (DE)

(72) Inventors: Vladimir Anferov, Bloomington, IN (US); Alexander Winnebeck, Bonn (DE)

(73) Assignees: VARIAN MEDICAL SYSTEMS, INC., Palo Alto, CA (US); VARIAN MEDICAL SYSTEMS PARTICLE THERAPY GMBH., Troisdorf (DE)

( * ) Notice: Subject to any disclaimer, the term of this patent is extended or adjusted under 35 U.S.C. 154(b) by 0 days.

(21) Appl. No.: 15/392,999

(22) Filed: Dec. 28, 2016

(65) Prior Publication Data

US 2018/0178038 A1 Jun. 28, 2018

(51) Int. Cl.
| | |
|---|---|
| *A61N 5/00* | (2006.01) |
| *A61N 5/10* | (2006.01) |
| *H05H 7/00* | (2006.01) |
| *H05H 7/04* | (2006.01) |

(52) U.S. Cl.
CPC ............ *A61N 5/1077* (2013.01); *A61N 5/00* (2013.01); *H05H 7/001* (2013.01); *H05H 7/04* (2013.01); *A61N 5/1081* (2013.01); *A61N 2005/1087* (2013.01); *H05H 2007/002* (2013.01); *H05H 2007/007* (2013.01); *H05H 2007/048* (2013.01)

(58) Field of Classification Search
USPC ...................................................... 250/492.3
See application file for complete search history.

(56) References Cited

U.S. PATENT DOCUMENTS

| | | | | |
|---|---|---|---|---|
| 8,264,174 | B2 * | 9/2012 | Liu | .......... H05H 15/00 250/396 R |
| 8,575,563 | B2 * | 11/2013 | Cameron | ............ A61N 5/1077 250/396 ML |
| 8,766,218 | B2 * | 7/2014 | Jongen | .................... A61N 5/10 250/492.3 |

(Continued)

FOREIGN PATENT DOCUMENTS

WO WO2011053960 5/2011

OTHER PUBLICATIONS

"Physical Specifications of Clinical Proton Beams from a Synchrotron" Arduni, et al. Published Oct. 5, 1995.

(Continued)

*Primary Examiner* — Phillip A Johnston

(57) ABSTRACT

A compact lightweight gantry for a proton therapy system that has a source-to-axis distance (SAD) of less than 2 m and can deliver a proton beam of superior quality. The reduced SAD leads to reduced requirements on the maximum magnetic fields that can be generated by the bend magnets in the gantry beamline. Correspondingly, lightweight bend magnets can be used. The various components in the gantry beamline are optimized to achieve a beam spot size of approximately 4 mm sigma or less through a pencil beam scanning nozzle disposed downstream of the final bending magnet. In addition, the proton therapy system is configured to operate at a maximum beam energy in the range of 220-230 MeV.

14 Claims, 5 Drawing Sheets

(56) References Cited

U.S. PATENT DOCUMENTS

| | | |
|---|---|---|
| 9,289,624 B2* | 3/2016 | Jongen ................... A61N 5/10 |
| 9,757,590 B2* | 9/2017 | Hiramoto ............. A61N 5/1048 |
| 2008/0023644 A1 | 1/2008 | Pedroni |
| 2014/0275699 A1 | 9/2014 | Benna et al. |

OTHER PUBLICATIONS

T. Norimine et al., "A Design of a Rotating Gantry With Easy Steering for Proton Therapy", Proceedings of EPAC 2002, Paris, France, Aug. 7, 2002, pp. 2751-2753.

\* cited by examiner

COMPACT LIGHTWEIGHT HIGH-PERFORMANCE PROTON THERAPY BEAMLINE

TECHNICAL FIELD

The present disclosure relates generally to the field of radiation therapy systems, and, more specifically, to the field of proton therapy systems.

BACKGROUND OF THE INVENTION

In a typical proton therapy system used for tumor radiation treatments for example, a proton beam is generated and output from an accelerator, e.g., a cyclotron or a synchrotron, with a certain initial energy. The initial energy determines a maximum penetration depth of the proton beam and typically is 235 MeV or higher. As the proton beam travels through a beam transportation system or a beamline, the beam energy is precisely tuned through energy selection mechanisms, e.g., an energy degrader or energy slit. The transport system includes a plurality of magnets for beam redirection (bending), focusing and steering. A rotational gantry equipped with a radiation nozzle is located at the end of the beam transport system. Eventually, the beam is delivered to a treatment station and irradiated onto a patient at an energy level prescribed for the specific treatment session based on the tumor volume, geometry, location and etc.

Due to the extremely high cost for purchasing and maintaining such a radiation system, a medical facility usually uses one accelerator for a plurality of treatment stations so the high expenditure for the accelerator facilities is distributed. Although using a multi-station single-cyclotron system is effective to distribute the cost for large medical facilities, the overall cost for such a multi-gantry system may be prohibitively high for smaller facilities that may only need one treatment station. Also, some multi-station systems do not support simultaneous treatment in multiple stations. This contribute to further disadvantage that a delay at one treatment station can cause delay at the other station. With the demand for proton beam radiation therapy increasing worldwide, smaller and less expensive proton therapy systems are highly desired to increase patient access to this treatment modality.

In proton radiation systems, including single and multi-station systems, the dipole magnets (or the bend magnets) in a gantry beamline consume significant expenditure associate with manufacture, installation, control, maintenance, and space that is limited and valuable in the medical facility.

In a gantry system, source-axis distance (SAD) refers to the distance from the iso-center to the effective source location of the proton beam. Typically, the iso-center corresponds to a center of an irradiated volume. If there are no beam focusing elements between the scanning magnets and the iso-center, the effective source location is the point where the beam changes the angle, i.e. the location of the scanning magnets. Conventionally, SAD greater than 2 m is considered necessary to achieve a parallel beam translation at the patient surface, especially in a scattering-based proton beam delivery system. A large SAD dictates a correspondingly large gantry radius, while increasing number of magnets and their complexity. Thus SAD has been the primary factor that drives the overall size and the weights of the constituents in a gantry beamline, which all contribute to the nearly prohibitive cost of manufacturing, transporting, assembling, installing, maintaining and operating such a proton therapy system.

FIG. 1 illustrates the configuration of a gantry beamline 100 in a proton radiation system with the SAD greater than 2 m in accordance with the prior art. The gantry is capable of rotating 360° around the iso-center 141. The gantry beamline 100 includes the first bend magnet 101 having an orbit bend angle of 45°, and the second bend magnet 102 having an orbit bend angle of 135°. Thus, the two bend magnets operate to bend a proton beam by 90° in total, e.g., from horizontal to vertical as illustrated.

A pencil beam scanning nozzle (not explicitly shown) may be coupled to the end of the second bend magnet 102 for delivering a dose of proton radiation to a patient. There are seven quadrupoles or focusing magnets 111-117 along the beamline 100, five of which 113-117 are disposed between the two bend magnets 101 and 102. In addition, several steering and correction magnets, e.g., 121-123, are installed between the focusing magnets 111-117. Each bend magnet 101 or 102 has an orbit bend radius of approximately 1.35 m. The second bend magnet 102 has an outer radius of approximately 1.26 m. The second bend magnet can generate a maximum magnetic field of approximately 1.8 Tesla.

The SAD 131 of this proton radiation system is approximately 2.1 m, from the center of the scanning system to the iso-center 141. Typically, a beam spot size of approximately 3-4 mm can be achieved at the iso-center. The end-to-end gantry length 132 measures approximately 9 m.

The second bend magnet 102 weighs about 22 tons, each quadrupole magnet weighs about 475 kg, and each scanning magnet weights about 1000 kg. The overall weight of such a gantry system exceeds 200 tons, including the tremendously heavy structure needed for supporting the gantry beamline.

A number of approaches have been developed or proposed for achieving a lightweight and compact gantry assembly. In one leading design on the market, the scanning system is moved upstream of the last gantry bend magnet. Such a gantry system can offer reasonably small footprints, unfortunately at considerable cost of beam precision, delivery accuracy, and many other aspects of system performance and treatment quality. In another design, reduction of gantry size is achieved by sacrificing full-range rotation of the gantry. For example the gantry can only rotate 220° instead of 360° as commonly needed for a treatment.

SUMMARY OF THE INVENTION

Accordingly, disclosed herein provide a compact lightweight gantry for a proton therapy system that offers superior beam delivery performance and yet preserves the capability of full-range rotation.

Embodiments of the present disclosure provide a proton therapy system including an optimized gantry beamline with a source-to-axis distance (SAD) of less than 2 m and preferably in the range of 1.1-1.8 m. The gantry beamline uses magnets that are much lighter and smaller than their conventional counterparts, including the bend magnets, the quadrupole magnets and the scanning magnets. Particularly, the final bend magnet is configured to generate a maximum magnetic field in the range of 1.45-1.55 Tesla.

The various components in the gantry beamline, and the spatial relation thereof, are optimized to achieve a beam spot size of approximately 4 mm or less through a pencil beam scanning nozzle that is disposed downstream of the final bending (second) magnet. Also, the proton therapy system may be configured to operate at a reduced maximum beam energy, preferably in the range of 220-230 MeV.

According to embodiments of the present disclosure, with a reduced SAD, a dose delivery nozzle positioned downstream of the final bend magnet, and optimization of the gantry beamline, the gantry length and diameter can be reduced significantly while maintaining high treatment quality. The optimized beamline design also leads to smaller and lighter magnets and improves beam transmission to the iso-center which may reduce the demand for heavy shielding of the treatment room. These improvements can significantly reduce equipment and facility costs. With lightweight magnets, the gantry can be configured to rotate 360° and maintain treatment precision, thus delivering the same treatment quality and workflow efficiency as much larger and more expensive conventional proton systems that have SAD greater than 2 m.

BRIEF DESCRIPTION OF THE DRAWINGS

Embodiments of the present invention will be better understood from a reading of the following detailed description, taken in conjunction with the accompanying drawing figures in which like reference characters designate like elements and in which.

DETAILED DESCRIPTION

Figure 1:
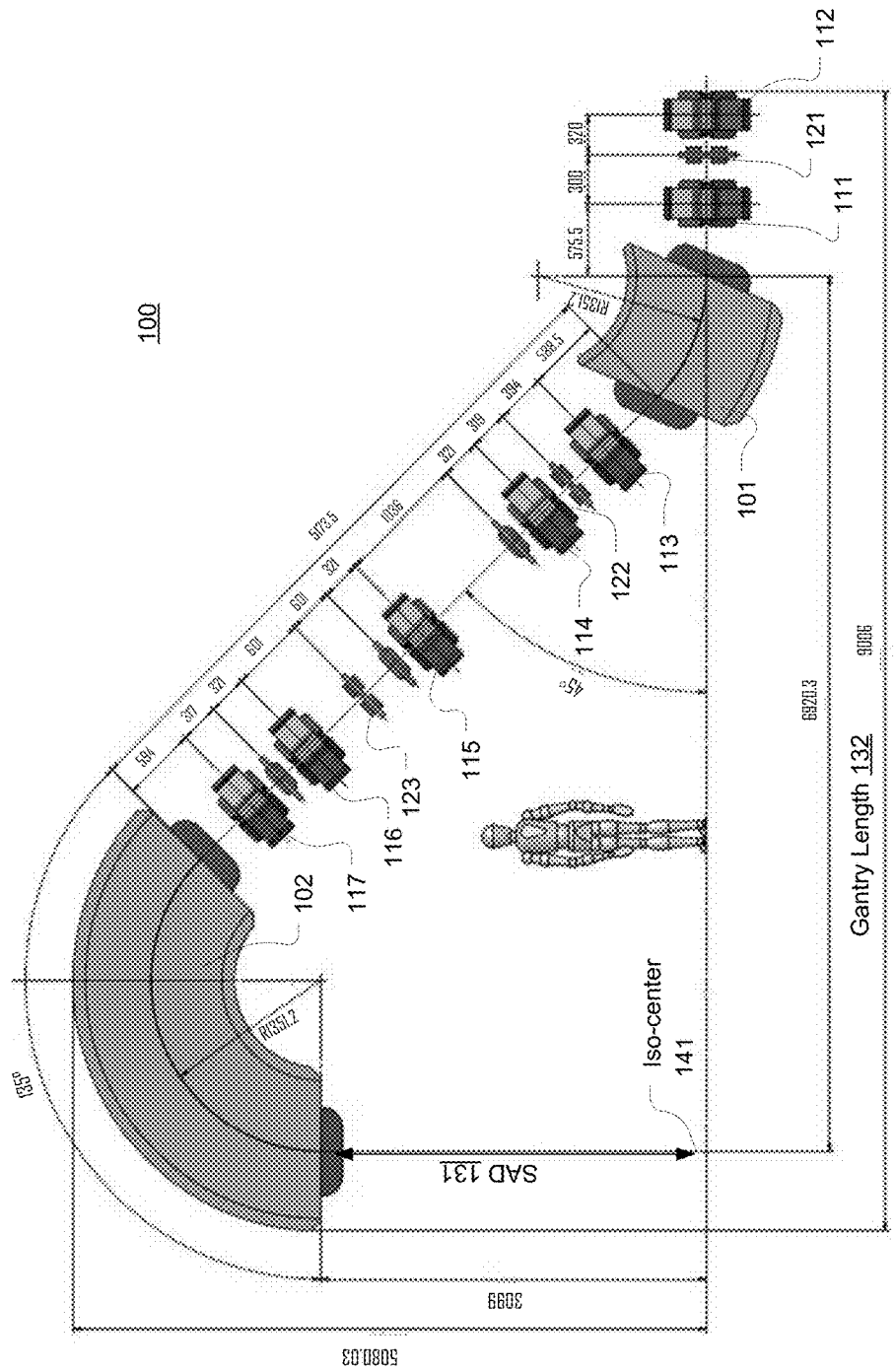
FIG. 1 illustrates the configuration of a gantry beamline in accordance with the prior art.

Reference will now be made in detail to the preferred embodiments of the present invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of embodiments of the present invention, numerous specific details are set forth in order to provide a thorough understanding of the present invention. However, it will be recognized by one of ordinary skill in the art that the present invention may be practiced without these specific details. In other instances, well-known methods, procedures, components, and circuits have not been described in detail so as not to unnecessarily obscure aspects of the embodiments of the present invention.

Although a method may be depicted as a sequence of numbered steps for clarity, the numbering does not necessarily dictate the order of the steps. It should be understood that some of the steps may be skipped, performed in parallel, or performed without the requirement of maintaining a strict order of sequence. The drawings showing embodiments of the invention are semi-diagrammatic and not to scale and, particularly, some of the dimensions are for the clarity of presentation and are shown exaggerated in the drawing Figures. Similarly, although the views in the drawings for the ease of description generally show similar orientations, this depiction in the Figures is arbitrary for the most part. Generally, the invention can be operated in any orientation.

Compact Lightweight High-Performance Proton Therapy Beamline

Overall, embodiments of the present disclosure provide a compact lightweight gantry for a proton therapy system that has a source-to-axis distance (SAD) of less than 2 m and can deliver a proton beam of superior quality. The reduced SAD leads to reduced requirements on the maximum magnetic fields that can be generated by the bend magnets in the gantry beamline. Correspondingly, lightweight bend magnets can be used. The various components in the gantry beamline are optimized to achieve a beam spot size of approximately 4 mm sigma or less through a pencil beam scanning nozzle disposed downstream of the final bending magnet. In addition, the proton therapy system is configured to operate at a maximum beam energy in the range of 220-230 MeV.

Figure 2:
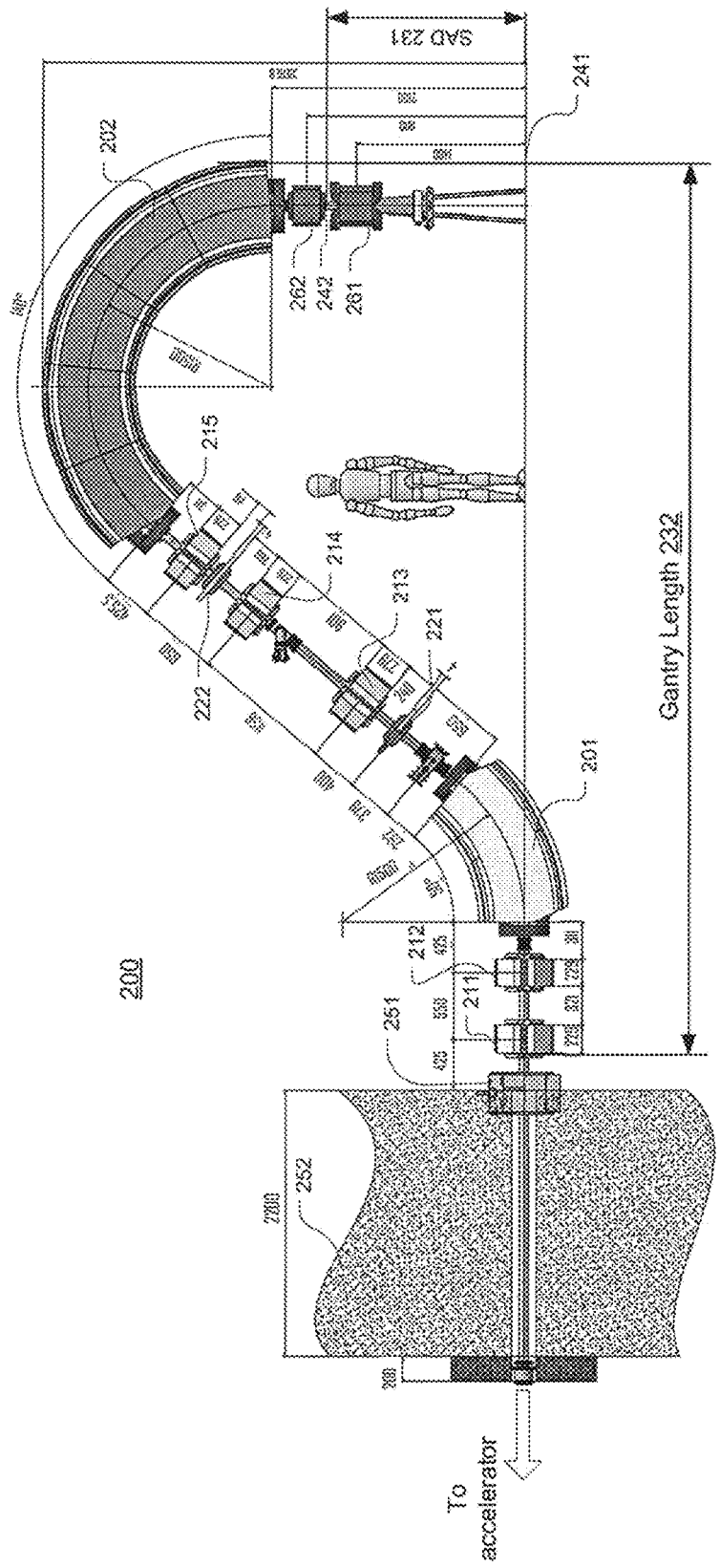
FIG. 2 illustrates the configuration of an exemplary gantry beamline in accordance with an embodiment of the present disclosure.

FIG. 2 illustrates the configuration of an exemplary gantry beamline 200 in a proton therapy system in accordance with an embodiment of the present disclosure. The gantry beamline 200 is coupled to an accelerator (not explicitly shown) through a main beamline.

The gantry beamline 200 is equipped with a pencil beam scanning nozzle configured to irradiate proton beam onto a target volume in a patient. The scanning magnets 261 and 262 in the pencil beam scanning nozzle are operable to control the lateral positions (X and Y) of the beam spot according to a predetermined scanning position (e.g., for spot scanning) or scanning path (e.g., for raster scanning). The gantry beamline further includes the first and the second (final) bend magnets 201 and 202, quadrupole magnets 211-215 serving as focusing magnets, and steering and correction magnets for centering the beam in the beamline, e.g., 221 and 222.

According to the present disclosure, the gantry beamline 200 has a source-axis distance (SAD) 231 of less than 2 m, which corresponds to the distance between the iso-center 241 and the effective center 242 of the scanning magnets 261 and 262. The effective center 242 may be located where the beam changes its angle in the pencil beam scanning nozzle. The SAD is preferably in the range of 1.1-1.8 m. In the illustrated example, the SAD is approximately 1.5 m. The distance between the end of the second bend magnet 202 and the iso-center 241 is approximately 2.1 m. There may be a gap of about 0.1 m interfacing the scanning magnet vacuum chamber with the gantry vacuum system.

Conventionally, the proton beam exiting the accelerator, e.g., a cyclotron or a synchrotron, has an initial energy of 250 MeV which can result in up to 40 cm proton beam penetration depth in water. However, in the vast majority of clinical applications, this penetration capability is excessive and the proton beam energy is usually attenuated to a much lower level before it is delivered to the patient. Thus, not only does the excessively high initial energy unnecessarily waste electrical power, but it also imposes requirements for heavier- and larger-than necessary magnets in the gantry beamline.

According to the present disclosure, the proton beam exiting the accelerator has an initial energy in the range of 220-230 MeV which is the maximum beam energy of the proton beam that can be used for dose delivery. Thus the initial beam energy is significantly lower than the level normally used in a conventional proton therapy system. This energy range still allows over 30 cm proton beam penetration depth in water, which is adequate for the vast majority of clinical applications. With the decreased initial energy of the proton beam, the magnetic fields used to direct the transportation of the proton beam can be advantageously reduced. Thus, the magnets in the gantry beamline can be much smaller and lighter compared with those used in a conventional proton therapy system.

The various magnets in the gantry beamline 200 can produce variable magnet fields. The magnets are configured to support small energy changes in 200 msec or less. For example, the magnet settings can be changed in step-wise fashion where each step corresponds to Bragg peak pull back of 5 mm range in water.

The first bend magnet 201 and the second bend magnet 202 operate to bend the proton beam by 90° in total from the direction in which the beam enters the gantry, e.g., a substantially horizontal direction. The first bend magnet 201 may have an orbit bend angle in the range of 40–55°, and the second bend magnet 202 may have an orbit bend angle in the range of 130-145°. In another embodiment, the first bend magnet 201 has an orbit bend angle of 50°, and the second bend magnet 202 has an orbit bend angle of 140°. The pencil beam scanning nozzle is disposed downstream of the second bend magnet 202.

The second bend magnet 202 is operable to generate a maximum magnetic field in the range of 1.45-1.55 Tesla, which is lower than that in a conventional gantry beamline 100 as shown in FIG. 1. Each of the bend magnets 201 and 202 has a bend radius of approximately 1.5 m. The cross-section of the second bend magnet 202 has an outer radius of approximately 0.36 m. Thus, the second bend magnet 202 has a smaller diameter and volume than its counterpart 102 in a conventional gantry beamline 100 as shown in FIG. 1. The second bend magnet 202 has a weight of approximately 7 tons in contrast with 20 tons as used in the conventional gantry beamline 100 in FIG. 1.

Due to reduction in SAD, the numbers of quadrupoles and other magnets needed in the gantry beam line can be decreased, which further contributes to a compact light-weight gantry design. In the illustrated example, only five quadrupole magnets 211-215 are used in the gantry beamline 200, in contrast with seven quadrupole magnets as used in the conventional gantry beamline 100 in FIG. 1. Three of the five quadrupole magnets 213-215 are installed between the first and the second bend magnets. Also, only two steering magnets 221 and 222 are used, instead of five or six as used in a conventional gantry beamline. In some embodiments, each quadrupole magnet 221 or 222 weighs approximately 250 kg in contrast with 475 kg as used in the conventional gantry beamline 100 in FIG. 1. For example, a quadrupole magnet 221 or 222 may have an inner bore of 78 mm.

During operation, the first pair of quadrupoles 211 and 212 prepare nearly a parallel beam in a vertical plane for optical transmission through the first bend magnet 201. At the same time, the beam is focused horizontally to match the dispersive region between the bend magnets 201 and 202. The triplet of quadrupoles 213-215 between the bend magnets 201 and 202 compensate the dispersion and make the beamline achromatic while providing the desired spot size at the iso-center 241 and point-to-point focusing. Edge angles of the second bend magnet 202 may be varied in conjunction with the triplet of quadrupoles 213-215 to achieve desired optical conditions.

The gantry beamline 200 has an end-to-end gantry length 232 of approximately 7.4 m, in contrast with 9 m as used in the conventional gantry beamline 100 in FIG. 1. About 30 cm distance in front of the first quadrupole may be reserved for interface between the concrete shielding wall 251 and the gantry rotating structure 252.

With the geometric optimization as described above and illustrated in FIG. 2, a beam spot size less than sigma 4 mm and beam position accuracy of 1 mm can be achieved in the proton therapy system. In some embodiments, the beam spot size can be sigma 3 mm or less. In some embodiments, the beam spot size can be sigma 3.45 mm, as presented in FIGS. 3A and 3B. With the configuration shown in FIG. 2, the gantry beamline 200 can also achieve variable beam spot size at the iso-center by selecting different source size at the entrance.

The gantry beamline 200 may also include various other components that are well known in the art, such as a vacuum system and an energy selection system (ESS) with an energy degrader. In addition, there may be in-situ beam diagnostic components used to monitor beam position and beam current.

The gantry beamline 200 is configured to rotate 360° around the iso-center. The beam spot can maintain its characteristics at the iso-center during the rotation.

Figure 3:
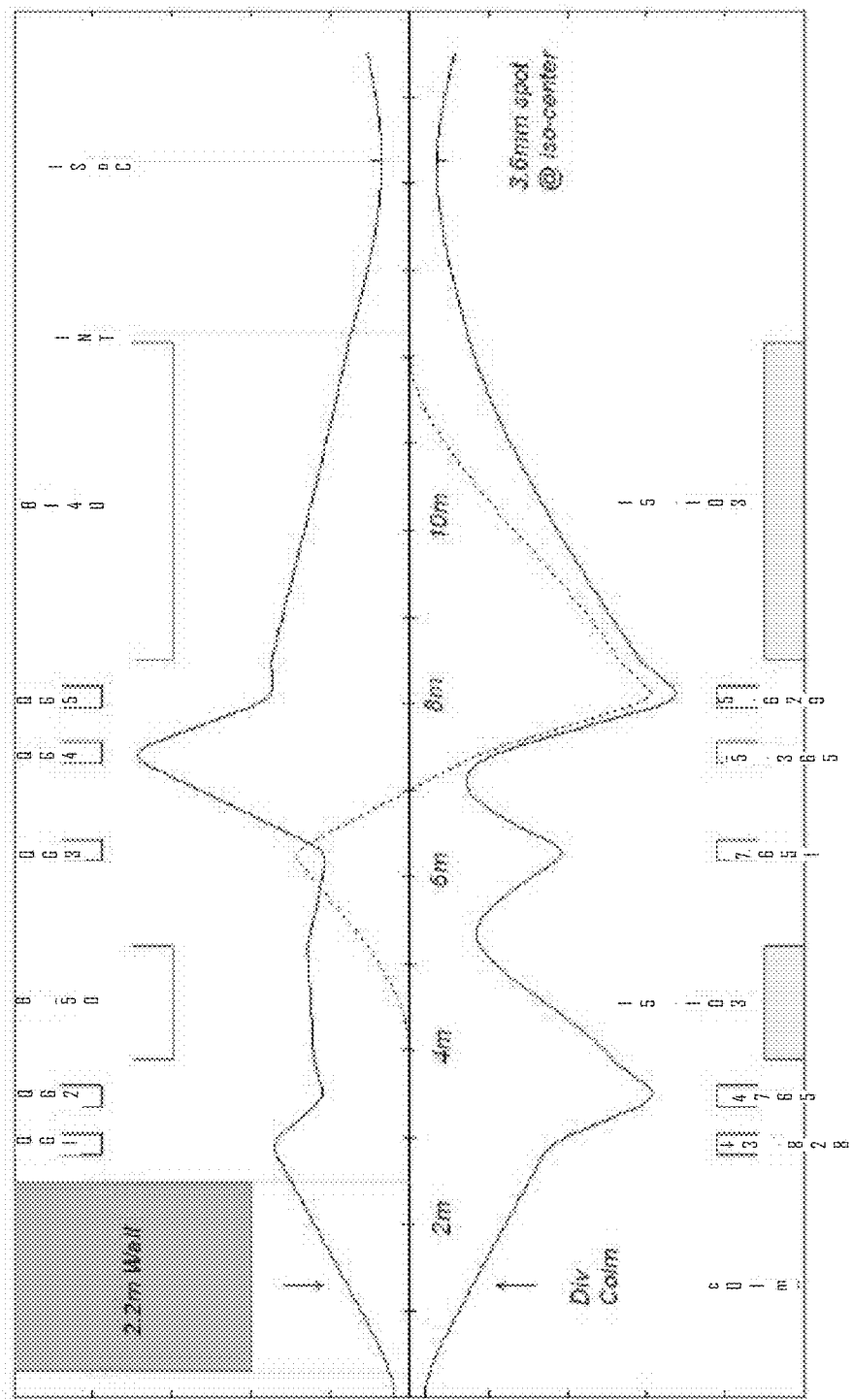
FIG. 3 shows sample vertical (top) and horizontal (bottom) beam envelopes that can be obtained using the exemplary gantry beamline illustrated in FIG. 2.

FIG. 3 shows sample vertical (top) and horizontal (bottom) beam envelopes along the exemplary gantry beamline in FIG. 2. As shown, the beam size varies along the beamline and good achromatic solution is obtained and dispersion is compensated at the nozzle. At the iso-center, the beam spot size is sigma 3.6 mm.

Figure 4:
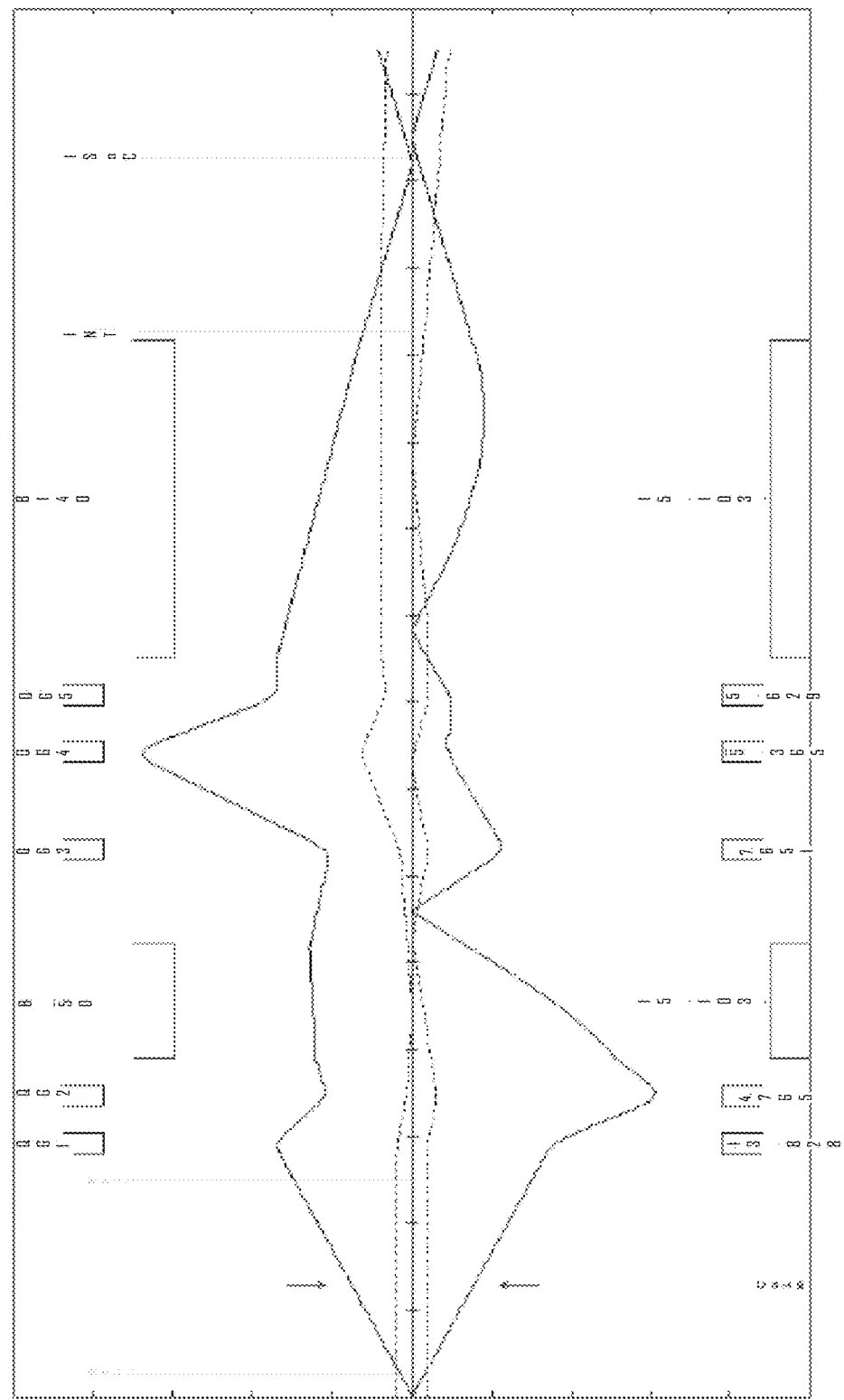
FIG. 4 shows sample sine and cosine cardinal trajectories in horizontal and vertical planes that can be obtained using the exemplary gantry beamline illustrated in FIG. 2.

FIG. 4 shows sample sine and cosine cardinal trajectories in the horizontal and vertical planes along the exemplary gantry beamline 200 in FIG. 2. These trajectories show that the gantry beamline 200 yields satisfactory point-to-point focusing. Thus, satisfactory beam focusing conditions at the iso-center may be achieved using approximate collimation of the degraded beam.

Figure 5A:
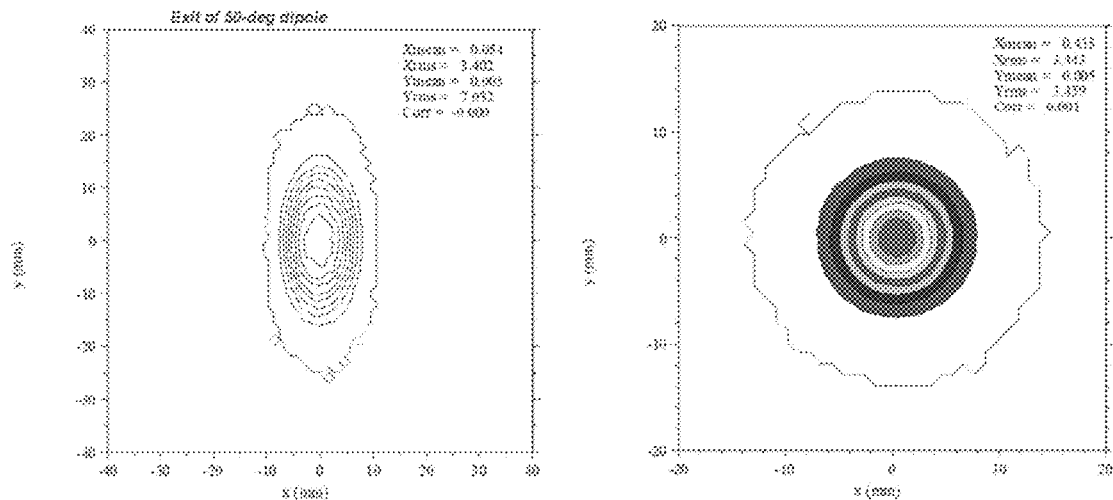
FIG. 5A shows simulated beam profiles at the exit of the first bend magnet (left) and at the iso-center (right) given ideal input conditions in the exemplary gantry beamline in FIG. 2.

FIG. 5A shows simulated beam profiles at the exit of the first bend magnet (left) and at the iso-center (right) given ideal input conditions in the exemplary gantry beamline 200 in FIG. 2. The beam profiles show that the beam is focused to a round beam spot with sigma 3.45 mm at the iso-center, and that the beam is focused horizontally near the exit of the first bend dipole.

Figure 5B:
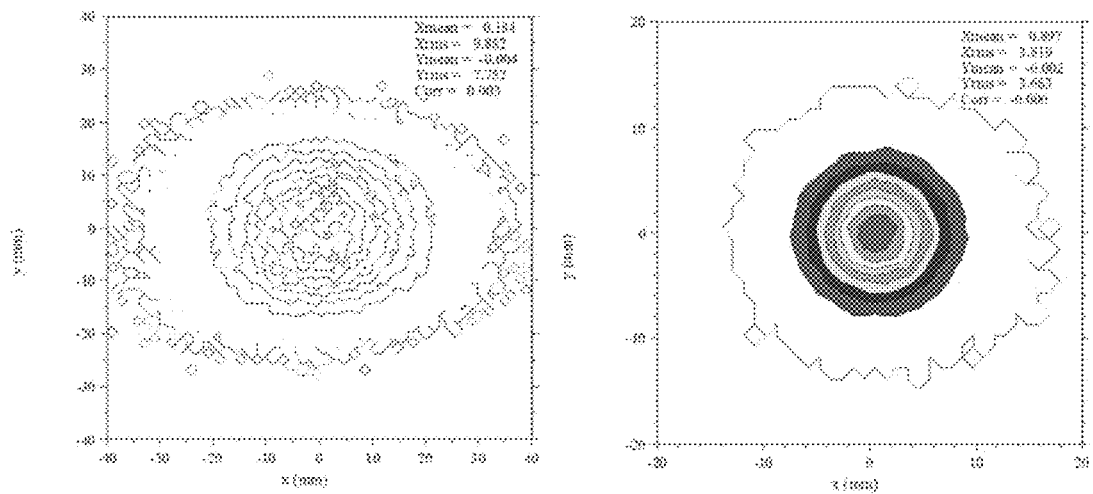
FIG. 5B shows simulated beam profiles at the exit of the first bend magnet (left) and at the iso-center (right) given the beam degraded to 80.1 MeV in the exemplary gantry beamline in FIG. 2.

FIG. 5B shows simulated beam profiles at the exit of the first bend magnet (left) and at the iso-center (right) given the beam degraded to 80.1 MeV in the exemplary gantry beamline 200 in FIG. 2. The profiles show that, due to momentum spread, the proton beam fills the beam pipe at the quadrupoles 213 and 215. The beam also fills the aperture of the quadrupole 214 vertically. Nonetheless, a well focused round beam is observed at the iso-center due to point-to-point focusing.

According to embodiments of the present disclosure, by reducing the SAD, positioning the nozzle downstream of the final bend magnet, and optimizing the gantry beamline, the gantry length and diameter can be reduced significantly while maintaining high treatment quality. The optimized beamline design also leads to smaller and lighter magnets and improves beam transmission to the iso-center which may reduce the demand for heavy shielding of the treatment room. These improvements can significantly reduce equipment and facility costs. With lightweight magnets, the gantry can be designed to rotate in a full range of 360° (e.g., ±180° or ±190°) and maintain treatment precision, thus delivering the same treatment quality and workflow efficiency, as much larger and more expensive conventional proton systems that have SAD greater than 2 m.

A gantry system in accordance with the present disclosure is compatible with a multi-room system configuration, as well as a single-room compact configuration, of a proton beam therapy system.

Although certain preferred embodiments and methods have been disclosed herein, it will be apparent from the foregoing disclosure to those skilled in the art that variations and modifications of such embodiments and methods may be made without departing from the spirit and scope of the invention. It is intended that the invention shall be limited only to the extent required by the appended claims and the rules and principles of applicable law.

What is claimed is:

1. A proton therapy system comprising:
   an accelerator configured to generate a proton beam with an initial energy; and
   a gantry assembly coupled to said accelerator, wherein a gantry length of said gantry assembly is less than 8 m and wherein said gantry assembly is configured to rotate 360°, said gantry assembly comprising:
      a scanning nozzle, wherein said scanning nozzle is configured to irradiate said proton beam to an object located proximate to an iso-center of said proton therapy system;
      two dipole magnets comprising a first dipole magnet and a second dipole magnet, wherein said second dipole magnet is operable to bend said proton beam in a bend radius of approximately 1.5 m, and wherein an outer radius of a cross section of said second dipole magnet is approximately 0.36 m; and
      five quadrupole magnets, wherein three of said five quadrupole magnets are disposed between said first dipole magnet and said second dipole magnet,
   wherein a source-to-axis distance (SAD) of said gantry assembly corresponds to a distance from said scanning nozzle to said iso-center and is less than or equal to 1.9 m, and wherein said proton therapy system is configured to deliver said proton beam with a beam spot at said iso-center that is less than sigma 4 mm.

2. The proton therapy system of claim 1, wherein a maximum magnetic field produced by said second dipole magnet is in the range of 1.45 Tesla to 1.55 Tesla.

3. The proton therapy system of claim 1, wherein said scanning nozzle comprises a pencil beam scanning nozzle disposed downstream of said second dipole magnet.

4. The proton therapy system of claim 2, wherein said second dipole magnet weighs less than 10 tons and wherein each of said five quadruple magnets weighs approximately 250 kg.

5. The proton therapy system of claim 1, wherein said first dipole magnet is operable to bend said proton beam by 50°, and wherein said second dipole magnet is operable to bend said proton beam by 140°.

6. The proton therapy system of claim 1, wherein said gantry assembly further comprises less than five steering magnets.

7. The proton therapy system of claim 1, wherein said beam spot size is sigma 3 mm or greater.

8. The proton therapy system of claim 1, wherein said initial energy is within a range between 220 MeV and 230 MeV.

9. A proton therapy system comprising:
   an accelerator configured to generate a proton beam with an initial energy;
   a gantry assembly coupled to said accelerator, wherein a gantry length of said gantry assembly is less than 8 m and wherein said gantry assembly is configured to rotate 360°, said gantry assembly comprising:
      two bend magnets comprising:
         a first bend magnet; and
         a second bend magnet disposed downstream of said first bend magnet, wherein said second bend magnet is operable to cause a bending radius of approximately 1.5 m, and wherein an outer radius of a cross section of said second bend magnet is approximately 0.36 m;
      five quadrupole magnets, wherein three of said five quadrupole magnets are disposed between said first bend magnet and said second bend magnet; and
      a scanning nozzle,
   wherein said second bend magnet is operable to generate a maximum magnetic field of less than or equal to 1.56 Tesla;
   wherein said scanning nozzle is disposed downstream of said first and said second bend magnets,
   wherein a source-to-axis distance (SAD) of said gantry assembly corresponds to a distance from said scanning nozzle to an iso-center of said proton therapy system and is less than or equal to 1.9 m, and
   wherein said proton therapy system is configured to deliver said proton beam with a beam spot at said iso-center that is less than sigma 4 mm, and wherein said proton therapy system is configured to deliver said proton beam with a position accuracy of 1 mm.

10. The proton therapy system of claim 9, wherein said maximum magnetic field is in the range of 1.45 Tesla to 1.55 Tesla.

11. The proton therapy system of claim 10, wherein said second bend magnet weighs less than 10 tons, and wherein each of said five quadrupole magnets weighs approximately 250 kg.

12. The proton therapy system of claim 9, wherein said gantry assembly further comprises less than 5 steering magnets.

13. The proton therapy system of claim 11, wherein said initial energy is within a range between 220 MeV and 230 MeV.

14. The proton therapy system of claim 1, wherein said proton therapy system is configured to deliver said proton beam with a position accuracy of 1 mm.

* * * * *